United States Patent [19]
Ribier et al.

[11] Patent Number: 6,051,250
[45] Date of Patent: Apr. 18, 2000

[54] PROCESS FOR THE STABILIZATION OF VESICLES OF AMPHIPHILIC LIPID(S) AND COMPOSITION FOR TOPICAL APPLICATION CONTAINING THE SAID STABILIZED VESICLES

[75] Inventors: Alain Ribier; Jean-Thierry Simonnet, both of Paris, France

[73] Assignee: L'Oreal, Paris, France

[21] Appl. No.: 08/195,025

[22] Filed: Feb. 14, 1994

[30] Foreign Application Priority Data

Feb. 12, 1993 [FR] France ................................ 93 01612

[51] Int. Cl.$^7$ .......................... A61K 9/127; A61K 7/00
[52] U.S. Cl. ........................ 424/450; 264/4.1; 264/4.3; 428/402.2; 514/844
[58] Field of Search ...................... 424/450, 401; 428/402.2; 264/4.1–4.6; 514/844

[56] References Cited

U.S. PATENT DOCUMENTS

| | | | |
|---|---|---|---|
| 4,670,185 | 6/1987 | Fujiwara | 252/311 |
| 4,708,861 | 11/1987 | Popescu | 424/1.1 |
| 4,830,857 | 5/1989 | Handjani | 424/450 |
| 5,008,109 | 4/1991 | Tin | 424/422 |
| 5,290,562 | 3/1994 | Meybeck | 424/450 |
| 5,332,595 | 7/1994 | Gaonkar | 426/602 |

FOREIGN PATENT DOCUMENTS

| | | |
|---|---|---|
| 0433131 | 6/1991 | European Pat. Off. . |
| 0437368 | 7/1991 | European Pat. Off. . |
| 0043327 | 1/1982 | France . |
| 2532191 | 3/1984 | France . |
| 2622104 | 4/1989 | France . |
| 2078543 | 1/1982 | United Kingdom . |
| 2079179 | 1/1982 | United Kingdom . |
| 2226002 | 6/1990 | United Kingdom . |

OTHER PUBLICATIONS

Kaoru, "Preparation of Heat–Resistant Emulsified Fat and Oil", Patent Abstracts of Japan, vol. 13, No. 208 (C–596) 1989 & JP–A–10 27 634.

*Primary Examiner*—Gollamudi S Kishore
*Attorney, Agent, or Firm*—Pillsbury Madison & Sutro LLP

[57] ABSTRACT

The invention relates to a process for stabilization of vesicles formed from a lipid-phase membrane containing at least one ionic and/or nonionic amphiphilic lipid encapsulating an aqueous phase, in the form of a dispersion in an aqueous phase, by addition of at least one stabilizing agent to the aqueous dispersion phase, in which the stabilizing agent (s) is/are chosen from the group composed of glycerol alginates, propylene glycol alginates, gellan gum and wellan gum. The invention also relates to a composition for topical application containing vesicles stabilized by the said process.

18 Claims, No Drawings

PROCESS FOR THE STABILIZATION OF VESICLES OF AMPHIPHILIC LIPID(S) AND COMPOSITION FOR TOPICAL APPLICATION CONTAINING THE SAID STABILIZED VESICLES

The present invention relates to a process for the stabilization of vesicles of amphiphilic lipid(s) and to a composition for topical application containing the said stabilized vesicles.

It is well known that some amphiphilic lipids are capable of forming vesicles in the presence of water. In a known manner, the vesicles consist of a membrane composed of one or more lipid lamellae encapsulating a phase which is generally aqueous. The lipid membrane is prepared from a lipid phase (termed vesicular phase) containing at least one ionic and/or nonionic amphiphilic lipid, and generally additives of a lipid nature capable of improving the stability of the vesicles and/or of decreasing their permeability; the vesicular lipid phase can also contain cosmetic and/or pharmaceutical active agents which are lipophilic. The encapsulated aqueous phase can also contain hydrophilic cosmetic and/or pharmaceutical active agents. The vesicles of amphiphilic lipid are generally prepared and used in the form of a dispersion in an aqueous dispersion phase. The aqueous dispersion phase can also contain hydrophilic active agents.

Vesicles of amphiphilic lipid(s) and processes for preparing them are described in many documents, especially in "Les Liposomes. Applications thérapeutiques" Technique et documentation ["Liposomes. Therapeutic applications" Technique and documentation]—Lavoisier 1985 and in "Liposomes en biologie cellulaire et pharmacologie" ["Liposomes in cell biology and pharmacology"], Edition INSERM, John Libbey Emotext 1987.

It has been proposed to use dispersions of vesicles of amphiphilic lipid(s) for the manufacture of cosmetic and/or pharmaceutical compositions. These compositions generally contain surfactants, more especially when they take the form of a cream or ointment; in effect, in this case, they contain a fatty phase which is generally emulsified using a surfactant.

Unfortunately, vesicles of amphiphilic lipid(s) have low stability in the presence of surfactants, and more especially in the presence of a surfactant and a fatty phase. In effect, surfactants invest the lipid-phase membrane until the said vesicles are converted into mixed micelles. This instability phenomenon of the vesicles increases with time and temperature. Thus, in compositions formulated in the form of an emulsion of a fatty phase, the incorporated vesicles of amphiphilic lipid(s) may be destroyed after a relatively short storage time, even before any use has been made. Many studies carried out by electron microscopy have, in effect, shown that, after a certain storage time, the presence of vesicles could no longer be detected.

The applicants have has found, as described, for example, in FR-A 2,490,504, that vesicles of amphiphilic lipid(s) are capable of maintaining oils, and, more generally, water-immiscible liquids, in the form of a stable dispersion in an aqueous phase without it being necessary to add emulsifying agents. Cosmetic compositions in which the vesicles are generally sufficiently stable are thereby obtained. However, in these compositions, the vesicles in the oily phase separate rapidly on application to the skin, and consequently the texture of these compositions is different from that of an emulsion. The sensation experienced by the users is hence different, and a large proportion of the latter retain their liking for the traditional texture of emulsions.

Moreover, many authors have recommended stabilizing vesicles in rigid matrices of aqueous gel. To this end, the use has been proposed of various gelling agents: polysaccharides, polypeptides, gelatin or agarose in the proportion of 0.5 to 10% by weight of the aqueous dispersion phase of the gel according to EP-A 0,162,724; gum arabic, sodium alginate, xanthan, collagen, polyacrylates or gelatin according to EP-A 0,172,907; high molecular weight DNA in the proportion of 0.1 to 10% by weight according to FR-A 2,668,063. However, these processes only enable compositions to be prepared in the form of rigid aqueous gels, which are not greatly liked from a cosmetic standpoint.

According to WO-A 87/01,587, to stabilize vesicles of amphiphilic lipid(s), they are sequestered in microcapsules consisting of an alginate salt and gelatin. Microcapsules are thereby obtained, which may be suspended in a continuous aqueous phase or an oily phase containing at least one emulsifying agent. This process for the stabilization of vesicles of amphiphilic lipid(s) is complicated, and consequently expensive. Furthermore, the properties of the vesicles of amphiphilic lipid(s) are masked by the microencapsulation layer.

In FR-A 2,622,104 and 2,645,455, a stabilization process is described in which the dispersion of vesicles is mixed with a mixed solution of a particular collagen, namely atelocollagen, and particular polysaccharides, namely glycosaminoglycans. This mixed solution is considered to be capable of protecting the vesicles of amphiphilic lipid(s) without a rigid gel being formed but, as it were, with coating of the vesicles taking place, thereby enabling the latter to be incorporated subsequently in cosmetic formulations containing a fatty phase, especially emulsions. However, this protection necessitates the use of relatively high proportions of stabilizing agent(s) relative to the vesicular lipid(s): according to Example 1, there is 0.5% of stabilizing agent for 1% by weight of lipid, equivalent to 50% of stabilizing agent relative to the lipid phase. This process hence possesses the drawback of profoundly modifying the characteristics specific to the lipid vesicles, which are thus masked by large amounts of stabilizing agent(s). In effect, it has been observed in the light microscope that the vesicles assume the appearance of clumps which have lost their own individuality. It has also been found that the addition of this type of stabilizing agent is not bereft of antigenicity.

Furthermore, it has been found that the addition of most known stabilizing agents does not have sufficient protective effect when the vesicles of amphiphilic lipid(s) are in the presence of the main surfactants commonly used in cosmetics.

According to the present invention, it was found that four types of gelling agent which had not hitherto been proposed for the stabilization of vesicles of amphiphilic lipid(s) could be used in a sufficiently small proportion relative to the lipid phase not to modify the intrinsic properties of the vesicles, and that, furthermore, they enabled the said vesicles to be stabilized even in the presence of surfactant(s). These gelling agents are glycerol alginates, propylene glycol alginates, gellan gum and welan gum.

The subject of the present invention is hence a process for stabilization of vesicles formed from a lipid-phase membrane containing at least one ionic and/or nonionic amphiphilic lipid encapsulating an aqueous phase, in the form of a dispersion in an aqueous phase, by addition of at least one stabilizing agent to the aqueous dispersion phase, characterized in that the stabilizing agent(s) is/are chosen from the group composed of glycerol alginates, propylene glycol alginates, gellan gum and welan gum.

Propylene glycol alginate has the formula (I) below:

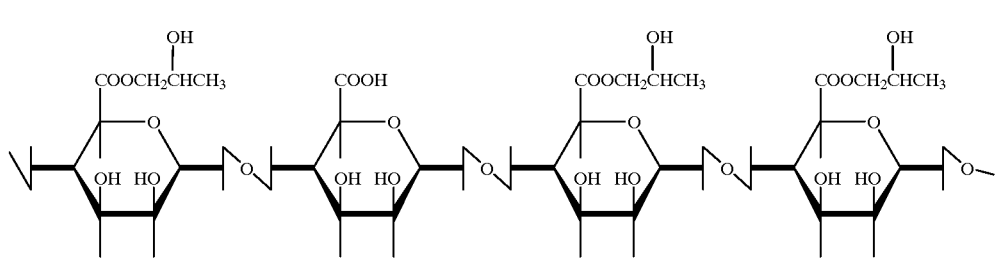

(I)

It is preferable to use alginates esterified to the extent of more than 60% with propylene glycol. Alginates having a smaller degree of esterification have a markedly weaker stabilizing action. The propylene glycol alginates esterified to the extent of 80–85% which are marketed under the tradenames "KELCOLOID O" or "MANUCOL ESTER E/PL" by the company "KELCO" are entirely suitable.

Glycerol alginate has the formula (I') below:

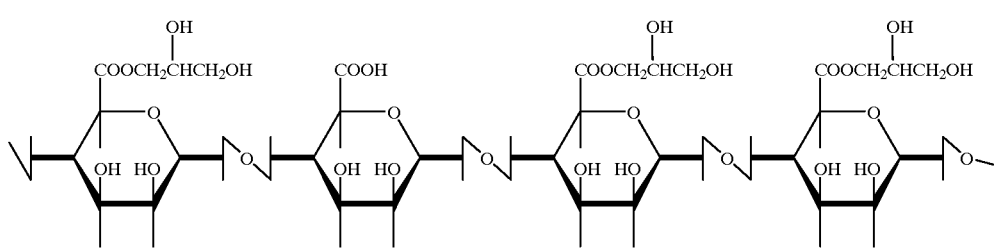

(I')

It is preferable to use glycerol alginates esterified to the extent of more than 60% with glycerol.

Gellan gum has a recurring tetrasaccharide structure composed of (glucose-glucuronic acid-glucose-rhamnose) units, and corresponds to the following formula II Gellan gum is generally prepared by submerged aerobic fermentation of Pseudomonas elodea. A gum of this type is marketed by the company "KELCO" under the tradename "KELCOGEL", and is entirely suitable. The purified gellan gum sold under the tradename "KELCOGEL PC (Personal Care)" by the company "KELCO" is also suitable.

Welan gum is a modified gellan gum. It has a recurring pentasaccharide structure composed of [glucose-glucuronic acid-glucose (rhamnose or mannose)-rhamnose] units, and corresponds to the following formula III

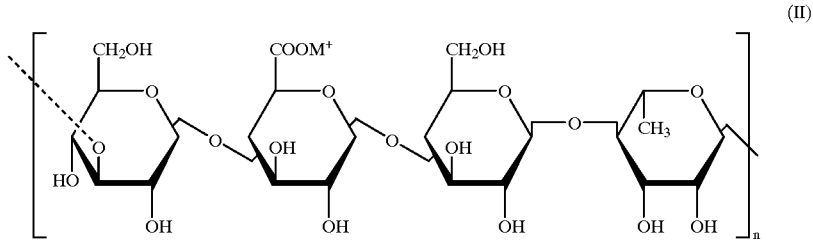

(II)

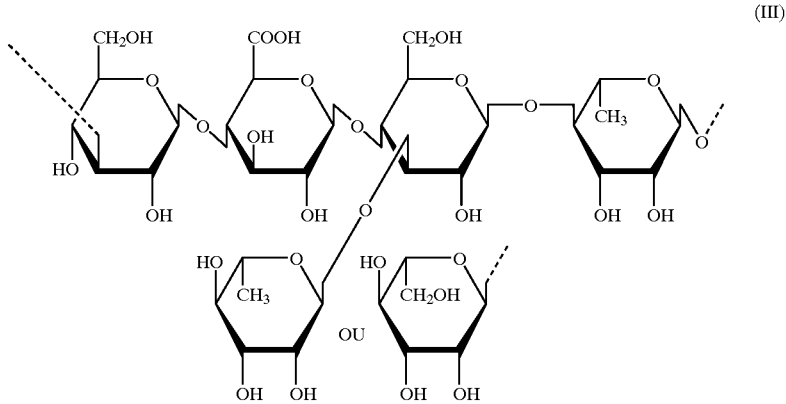

(III)

It is prepared, in general, by fermentation of Alcaligenes strain ATCC 31 555. A gum of this type is marketed by the company "KELCO" under the tradename "K 1 A 96", and is entirely suitable.

The stabilizing agents according to the invention are used in the proportion of 0.1 to 20% by weight relative to the weight of the vesicular lipid phase. With amounts above 20%, there is a risk of the intrinsic properties of the vesicles being modified and of the gel becoming rigid, and with ratios of less than 0.1%, a sufficient protective effect is no longer observed. The preferred ratio according to the invention is between 0.2 and 10%; it is more especially in the region of 2% by weight of stabilizing agent(s) relative to the weight of the vesicular lipid phase.

The above stabilizing agents are commonly used in food for human consumption, and have the advantage of not possessing antigenicity.

The above stabilization process has the advantage of permitting the stabilization of vesicles even in a composition containing a surfactant and/or a fatty phase. It was found that an aqueous composition containing an aqueous dispersion of vesicles containing up to 20% by weight of surfactant relative to the total weight of the composition was stable. Furthermore, the vesicles remain stable when the fatty phase combined with the aqueous dispersion phase represents up to 50% by weight relative to the total weight of the composition, in the presence of surfactants other than the lipids of which the vesicles are composed.

When the compositions contain a fatty phase, the latter can be any fatty phase generally used for the preparation of cosmetic or pharmaceutical compositions for topical application in the form of an ointment, cream, lotion or milk. The surfactant can be any surfactant used for the preparation of cosmetic or pharmaceutical compositions in the form of a water-in-oil or oil-in-water type emulsion of a fatty phase. A suitable stabilization may be obtained with the amounts of surfactant and/or of fatty phase generally used for the manufacture of cosmetic or pharmaceutical compositions for topical application.

According to the invention, it is possible to stabilize all known vesicles of lipid phase, irrespective of whether they are prepared from ionic and/or nonionic amphiphilic lipid (s).

The present invention also relates to a composition containing a dispersion of lipid-phase vesicles which are stabilized by the process described above.

The subject of the present invention is hence also a composition for topical application, in particular a cosmetic or pharmaceutical composition, containing, in the first place, a dispersion of vesicles formed from a lipid-phase membrane containing at least one ionic and/or nonionic amphiphilic lipid encapsulating an aqueous phase, dispersed in an aqueous phase, and, in the second place, at least one agent that stabilizes the said vesicles, characterized in that the stabilizing agent(s) is/are chosen from the group composed of glycerol alginates, propylene glycol alginates, gellan gum and welan gum.

In the composition according to the invention, the alginates are preferably alginates esterified to the extent of at least 60% with propylene glycol or glycerol.

The stabilizing agent(s) represent(s) from 0.1 to 20% by weight relative to the weight of the vesicular lipid phase, and preferably from 0.2 to 10%.

The compositions according to the invention can contain up to 20% by weight of surfactant(s) relative to the total weight of the composition. The surfactant(s) preferably represent(s) from 1 to 20% by weight relative to the total weight of the composition.

The surfactants which are usable can be, in a known manner, chosen from nonionic, anionic, cationic or amphoteric amphiphilic compounds such as, for example, sodium alkyl sulphates, polyol esters, oxyethylenated or otherwise, such as, for example, esters of glycerol, of sorbitol and of sorbitol anhydride; polyoxyethylenated alcohols; polypropylenated alcohols; and polyoxyethylene/polyoxypropylene copolymers. As a sodium alkyl sulphate, sodium lauryl sulphate may be mentioned. As polyol esters, there may be mentioned polyoxyethylene stearates such as the products sold under the tradenames "MYRJ 52" or "MYRJ 53" by the company "ICI", as well as oxyethylenated mixtures of sorbitol stearate such as the products sold under the tradenames "TWEEN 20" and "TWEEN 60" by the company "ICI". As a polyoxyethylenated alcohol, the polyethylene glycol ether of stearyl alcohol, such as the product sold under the tradename "BRIJ 72" by the company "ICI", may be mentioned. As a polypropylenated alcohol, the polypropylene glycol ether of stearyl alcohol, such as the product sold under the tradename "ARLAMOLE E" by the company "ICI", may be mentioned. As a polyoxyethylene/ polyoxypropylene copolymer, the product sold under the tradename "POLOXAMER 188" by the company "ICI" may be mentioned. The dispersion of lipid-phase vesicles used for the preparation of the composition according to the invention can be any known dispersion of vesicles.

The lipid phase of which the membranes of the vesicles of the dispersion are composed can hence comprise, in a known manner, at least one lipid chosen from the group composed of:

A) the nonionic lipids defined below:
(1) linear or branched glycerol derivatives of formula $$R_oO \text{---} [C_3H_5(OH)O]_{\overline{n}} \text{---} H \qquad (IV)$$

in which formula (IV):
—$C_3H_5(OH)O$— is represented by the following structures, taken mixed or separately:

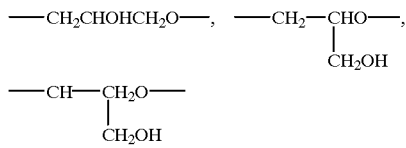

$\overline{n}$ is an average statistical value between 1 and 6, or alternatively n=1 or 2 and —$C_3H_5(OH)O$— is then represented by the structure —$CH_2CHOH$—$CH_2O$—;

$R_o$ represents:
   (a) a saturated or unsaturated, linear or branched aliphatic chain containing from 12 to 30 carbon atoms; or hydrocarbon radicals of lanolin alcohols; or long-chain alpha-diol residues;
   (b) a residue $R_1CO$, where $R_1$ is a linear or branch $C_{11}$–$C_{29}$ aliphatic radical;
   (c) a residue $$R_2 \text{---} [OC_2H_3(R_3)]\text{---}$$

where:
   $R_2$ can assume the meaning (a) or (b) given for $R_o$;
   —$OC_2H_3(R_3)$— is represented by the following structures, taken mixed or separately:

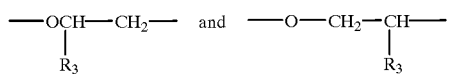

where $R_3$ assumes the meaning (a) given for $R_o$;
(2) linear or branched polyglycerol ethers containing two fatty chains;
(3) fatty-chain diols;
(4) fatty alcohols, oxyethylenated or otherwise, sterols such as, for example, cholesterol and phytosterols, oxyethylenated or otherwise;
(5) polyol ethers and esters, oxyethylenated or otherwise, the sequence of the ethylene oxide groups being linear or cyclic ; polyol esters are understood, in particular, to mean esters of at least one polyol, chosen from the group composed of ethylene oxides, sorbitan, sorbitan bearing 2 to 60 ethylene oxide units, glycerol bearing 2 to 30 ethylene oxide units, polyglycerols containing 2 to 15 glycerol units, sucroses and glucoses bearing 2 to 30 ethylene oxide units, and at least one fatty acid containing a saturated or unsaturated, linear or branched $C_5$–$C_{17}$ alkyl chain, the number of alkyl chains per polyol group being between 1 and 10;
(6) glycolipids of natural or synthetic origin, ethers and esters of mono- or polysaccharides, and in particular glucose ethers and esters;
(7) the hydroxyamides described in French Patent No. 2,588,256 and represented by the formula:

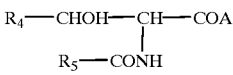

in which formula (V):
   $R_4$ denotes a $C_7$–$C_{21}$ alkyl or alkenyl radical;
   $R_5$ denotes a saturated or unsaturated $C_7$–$C_{31}$ hydrocarbon radical;
   COA denotes a group chosen from the following two groups:
      a residue

where:
      B is an alkyl radical derived from mono- or polyhydroxylated primary or secondary amines; and
      $R_6$ denotes a hydrogen atom or a methyl, ethyl or hydroxyethyl radical; and
      a residue —COOZ, where Z represents the residue of a $C_3$–$C_7$ polyol;
(8) natural or synthetic ceramides;
(9) dihydroxyalkylamines, oxyethylenated fatty amines;
(10) the glycerol derivatives described in International Application PCT No. 91/00,889 filed on 13th November 1991, and corresponding to the formula:

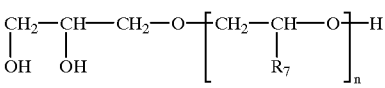

in which formula (VI) $R_7$ represents a linear $C_{14}$ to $C_{18}$ alkyl radical or a group —$CH_2A$ in which A is —$OR_{14}$ , $R_{14}$ representing a linear $C_{10}$–$C_{18}$, and preferably $C_{16}$, alkyl radical, and n represents an average statistical value greater than 1 and equal to not more than 3, and, in addition, when $R_7$=—$CH_2A$, n can also represent an actual (non-statistical) value equal to 2;

B) the ionic amphiphilic lipids defined below:
(1) anionic amphiphilic lipids chosen from the group composed of:
   natural phospholipids, in particular egg or soya bean lecithin, or sphingomyelin, chemically or enzymatically modified phospholipids, in particular hydrogenated lecithin, and synthetic phospholipids, in particular dipalmitoylphosphatidylcholine;
   anionic compounds, such as those described in French Patent No. 2,588,256 and represented by the formula:

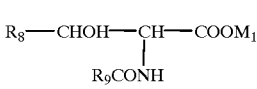

in which formula (VII):
   $R_8$ represents a $C_7$–$C_{21}$ alkyl or alkenyl radical,
   $R_9$ represents a saturated or unsaturated $C_7$–$C_{31}$ hydrocarbon radical, and
   $M_1$ represents H, Na, K, $NH_4$ or a substituted ammonium ion derived from an amine;

(2) anionic compounds chosen from the group composed of: phosphoric esters of fatty alcohols, for example dicetyl phosphate and dimyristyl phosphate in the form of acids or of alkali metal salts; heptylnonylbenzenesulphonic acid; cholesterol acid sulphate and its alkali metal salts and cholesterol acid phosphate and its alkali metal salts; lysolecithins; alkyl sulphates, for example sodium cetyl sulphate; gangliosides; lipoamino acids and/or lipoamino salts, in particular mono- and disodium acylglutamates; phosphatidic acid and its alkali metal salts;

(3) cationic amphiphilic lipids chosen from the group composed of:

cationic compounds which are quaternary ammonium derivatives, corresponding to the formula:

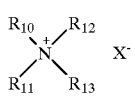

(VIII)

with $R_{10}$ and $R_{11}$, which may be identical or different, representing $C_{12}$–$C_{20}$ alkyl radicals, and $R_{12}$ and $R_{13}$, which may be identical or different, representing $C_1$–$C_4$ alkyl radicals;

long-chain amines and their quaternary ammonium derivatives, esters of long-chain amino alcohols and their salts and quaternary ammonium derivatives;

the prepolymerized amphiphilic lipids obtained, in particular, from polymerizable lipids given on page 129 of "Angewandte Chemie" Vol. 27 No. 1, January 1988, or from the products of reaction of an anionic lipid and a polymerizable cationic compound as described on page 137 of the above reference.

Various lipophilic additives, especially cosmetic and/or pharmaceutical active agents, may be added in a known manner to the vesicular lipid phase.

Also in a known manner, the encapsulated aqueous phase of the vesicles and/or the aqueous dispersion phase can contain hydrophilic additives, especially cosmetic and/or pharmaceutical active agents.

The aqueous dispersion phase can, in a known manner, consist of water or a mixture of water and at least one water-miscible solvent such as $C_1$–$C_7$ alcohols and $C_1$–$C_5$ alkyl polyols.

The composition advantageously contains a fatty phase combined with the aqueous dispersion phase.

This fatty phase can consist of at least one oil in the form of droplets dispersed in the aqueous phase of dispersion of the lipid-phase vesicles, the dispersion of droplets being stabilized in a known manner by the lipid-phase vesicles; it is also possible to use at least one emulsifying agent in order to provide the dispersion of droplets with additional stabilization.

This fatty phase is preferably in the form of a water-in-oil or oil-in-water type emulsion, the aqueous phase of the emulsion consisting at least partially of the aqueous phase of dispersion of the vesicles. The fatty phase can be any phase generally used in cosmetics or in pharmacy for the preparation of ointments, creams, milks or lotions which are usable by topical application. Among the compounds which are usable in the fatty phase, there may be mentioned:

oils and fats of animal or vegetable origin composed of esters of a fatty acid and of polyols, especially triglycerides, for example sunflower, maize, soya bean, gourd, grape-pip, jojoba, sesame and hazelnut oils, fish oils, glycerol tricaproprylate, or vegetable or animal oils of formula $R_{14}COOR_{15}$, in which formula $R_{14}$ represents the residue of a higher fatty acid containing from 7 to 19 carbon atoms and $R_{15}$ represents a branched hydrocarbon chain containing from 3 to 20 carbon atoms, for example Purcellin oil;

natural or synthetic essential oils such as, for example, eucalyptus, lavandin, lavender, vetiver, Litsea cubeba, lemon, sandalwood, rosemary, chamomile, savory, nutmeg, cinnamon, hyssop, caraway, orange, geraniol, cade and bergamot oils;

hydrocarbons such as hexadecane and liquid petrolatum;

halocarbons, in particular fluorocarbons such as fluoroamines, for example perfluorotributylamine, fluorinated hydrocarbons, for example perfluorodecahydronaphthalene, fluoro esters and fluoro ethers;

waxes;

silicones, for example polysiloxanes, polydimethylsiloxanes and fluorosilicones;

esters of an inorganic acid and an alcohol, and ethers and polyethers.

The fatty phase generally represents from 5 to 50% by weight relative to the total weight of the composition.

The composition can contain, in a known manner, at least one lipophilic or hydrophilic cosmetic and/or pharmaceutical active agent. When they are lipophilic, the active agents may be introduced into the fatty phase and/or, in a known manner, into the lipid phase of which the membrane of the vesicles is composed. When these active agents are hydrophilic, they may be introduced into the encapsulated aqueous phase of the vesicles and/or into the aqueous phase of dispersion of the vesicles. Amphiphilic active agents may also be used, these active agents being capable of distributing themselves both in the lipid or fatty phase and in the aqueous phase.

As a guide, a non-limiting list of the active agents which are usable in the compositions according to the invention is given below in Table I.

TABLE I

| FUNCTION | ACTIVE AGENTS WHICH ARE USABLE |
|---|---|
| Antioxidant or anti-free-radical | Extracts of the following plants: Hawthorn. Ginkgo biloba. Green tea. Vine. Rosemary. Enzymes: Marketed by SEDERMA under the name SB 12, and consisting of a mixture of lactoferrin and lactoperoxidase, glucose oxidase and potassium thiocyanate. Superoxide dismutase. Glutathione peroxidase. Superphycodismutase extracted from algae. Coenzymes Q, especially coenzyme Q10. Sequestering agents, especially polyphosphonic acid derivatives. Tannins. Selenium and its derivatives, especially selenomethionine. Peptides, for example a mixture of spleen and thymus extracts. Thiolim and unstabilized bovine serum albumin. Proteins, for example haemocyanin, which is a copper-containing protein extracted from marine snails, and apohaemocyanin, which is a similar protein without copper. |

TABLE I-continued

| FUNCTION | ACTIVE AGENTS WHICH ARE USABLE |
|---|---|
| | Flavonoids, in particular catechin, proanthocyanidins, flavanols, flavones, isoflavones, flavanenols, flavanones, flavans and chalcones. |
| | Carotenoids, in particular β-carotene and annatto. |
| | Sorbohydroxyamic acid. |
| | Tocopherols, in particular alpha-tocopherol and alpha-tocopherol acetate. |
| | Ascorbyl palmitate. |
| | Propyl gallate. |
| | Caffeic acid and its derivatives. |
| | Ascorbic acid. |
| | Homogentisic acid. |
| | Erythorbic acid. |
| | Nordihydroguaiacetic acid. |
| | Lysine laurylmethionate. |
| | Butylated hydroxyanisole |
| | Butylated hydroxytoluene. |
| | "SOD-like" substances. |
| Hydrating or humectant | A reconstitution of sweat ("Normal moisturizing factors" NMF). |
| | Sodium pyroglutamate. |
| | Hyaluronic acid. |
| | Chitosan derivatives (carboxymethylchitin). |
| | β-Glycerophosphate. |
| | Lactamide. |
| | Acetamide. |
| | Ethyl, sodium and triethanolamine lactates. |
| | Metal pyrrolidonecarboxylates, especially those of Mg, Zn, Fe, Ca or Na. |
| | Thiamorpholinone. |
| | Orotic acid. |
| | alpha-Hydroxylated $C_3$ to $C_{20}$ carboxylic acids, in particular alpha-hydroxypropionic acid. |
| | Polyols, in particular inositol, glycerol, diglycerol, sorbitol. |
| | Polyol glycosides, in particular alginate and guar. |
| | Proteins, in particular gelatin and soluble collagen. |
| | Lipoprotides chosen from mono- or polyacylated derivatives of amino acids or of polypeptides in which the acid residue RCO contains a $C_{13}$–$C_{19}$ hydrocarbon chain, in particular palmitoylcaseinic acid, palmitoylcollagenic acid, the O,N-dipalmitoyl derivative of hydroxyproline, sodium stearoylglutamate, collagen stearoyl tripeptide, collagen oleyl tetra- and pentapeptide, hydroxyproline linoleate. |
| | Urea and its derivatives, in particular methylurea. |
| | Skin tissue extract, in particular that marketed by Laboratoires Serobiologiques de Nancy (LSN) under the name "OSMODYN" and containing peptides, amino acids, saccharides and 17% of mannitol. |
| | More especially, a combination of glycerol, urea and palmitoylcaseinic acid. |
| Melanoregulator: | Bergamot and citrus oils. |
| 1) suntan accelerator | alpha-MSH and itu synthetic homologues. Caffeine. Tyrosine derivatives, in particular glucose tyrosinate and N-malyltyrosine. |
| 2) Depigmenting | Ascorbic acid or vitamin C and its derivatives, in particular Mg ascorbyl phosphate. |
| | Hydroxy acids, in particular glycolic acid. |
| | Kojic acid. |
| | Arbutin and its derivatives; |
| | Haemocyanin (copper-containing protein of the marine snail) and apohaemocyanin (protein similar to the above without copper). |
| | Hydroquinone and its derivatives, in particular the manoalkyl ether and the benzyl ether |
| Skin coloration (artificial suntan) | ortho-Diacetylbenzene. Indoles. Dihydroxyacetone. Erythrulose. Glyceraldehyde. gamma-Dialdehydes, in particular tartraldehyde. |
| Liporegulators | Complexes of vitamins and trace elements, in particular the vitamin $B_6$/zinc complex. |
| (slimming and antiacne, antiseborrhoea) | Orizanol. Azelaic acid. Xanthines and alkylxanthines, in particular extract of cola, caffeine and theophylline. Cyclic and acyclic adenosine monophosphate. Adenosine triphosphate. Ivy extract. Horse chestnut extract. Extracts of algae, in particular extract of red algae (Fucus serratus) and cytofiltrate. Ginseng extract. Centella asiatica extract (asiaticoside) containing genin and asiatic acid. Thioxolone (HBT). S-Carboxymethylcysteine. S-Benzylcysteamine. |
| Anti-ageing and anti-wrinkle | Unsaponifiables, for example of soya bean and avocado. Unsaturated fatty acids, in particular linoleic acid and linolenic acid. Hydroxy acids, in particular glycolic acid. Growth factors. Trace element/vitamin complexes, in particular $B_6$/Zn. 5-n-Octanoylsalicylic acid. Adenosine. Retinol and its derivatives, in particular retinol acetate and retinol palmitate. Retinoids, in particular cis- or trans-retinoic acids and those described in Patents FR-A-2,570,377; EP-A-199,636; and EP-A-325,540 and European Patent Application 90-402072. Combination of retinoids and xanthines. Hydroxyproline. Sialic acids. The unstabilized extract of spleen, of thymus, Thiolim and bovine serum albumin sold by the company "SILAB" under the trade name "SILAB". An animal placental extract, in particular 5.5% bovine placental embryonic extract in water, stabilized with 0.2% of exyl K100a (matrix). Proteoglycans, especially stabilized 5% bovine tracheal cartilage proteoglycan (proteodermin). Colostrum. Cell oxygenation factors, in particular octacosamol. |
| Anti-UV | UV screening agents, in particular 2-ethylhexyl para-methoxycinnamate; benzophenone, benzylidenecamphor and their derivatives, especially 2,2', 4,4'-tetrahydroxybenzophenone and 2-hydroxy-4-methoxybenzophenone-5-sulphonic acid; para-aminobenzoic acid, dipropylene glycol salicylate, octyl salicylate, the dibenzoylmethane derivatives sold under the brand names EUSOLEX 8020 or PARSOL 1789 and the products sold under the brand names EUSOLEX 232, UNIVUL T 150, UNIZVUL N 539, ESCALOL 507. |
| Keratolytic | Salicylic acid and its derivatives such as alkylsalicylic acids, in particular 5-n-octanoyl- and 5-n-dodecanoylsalicylic acids, N-hexadecylpyridinium salicylate. Retinoic acid. Proteolytic enzymes, in particular trypsin, alpha-chymotrypsin, papain, bromelain and pepsin. Benzoyl peroxide. Urea. alpha-Hydroxy acids. |
| Emollient | Esters such as isopropyl adipate. |
| Anti-inflammatory | Corticoids such as β-methasone 17-acetate, indomethacin, ketoprofen, flufenamic acid, ibuprofen, diclofenac, diflunisal, fenclofenac, naproxen, piroxicam and sulindac. |

TABLE I-continued

| FUNCTION | ACTIVE AGENTS WHICH ARE USABLE |
| --- | --- |
|  | Glycerol monostearyl ether (batyl alcohol) and glycerol nonocetyl ether (chimyl alcohol). Glycyrrhetinic acid and its salts, in particular the ammonium salt. alpha-Bisabolol (chamomile extract). Shikonin. Extracts of plants such as arnica, aloe, cornflower water. Extracts of meristematic tissue, in particular oak root extract. Plankton. |
| Cooling | Menthol. Menthyl lactate. |
| Cicatrizing | Skin tree, mimosa tenui flora extract. Centella asiatica extract. β-Glycyrrhetinic acid. Hydroxyproline. Arginine. A placental extract. A yeast extract. Fagaramide. N-Acetylhydroxyproline. Acexamic acid and its derivatives. |
| Vasoprotective | Flavonoida, in particular rutin derivatives such as etoxazorutin and sodium rutin propylsulphonate. Plant extracts, in particular Ginkgo biloba oily extract and extract of horse chestnut (escin), of ivy (saponins) and of butcher's broom. alpha-Tocopherol nicotinate. |
| Antibacterial, antifungal | Trimethylcetylammonium bromide. Sorbic acid. Benzoyl peroxide. Cetylpyridinium chloride. Benzalkonium chloride. para-Hydroxybenzoic acid and its salts. 2-Bromo-2-nitro-1,3-propanediol. 3,4,4'-Trichlorocarbanilide. 2,4,4'-Trichloro-2-hydroxydiphenyl ether. Dehydroacetic acid. A grapefruit extract in glycerol and propylene glycol. Chlorhexidine. Hexetidine. Hexamidine. |
| Insect-repellent agent | Dimethyltoluamide. |
| Antiperspirant | Aluminium chlorohydrate. Aluminium chloride. Sodium lactate/aluminium chlorohydroxy complex. Zirconyl chlorohydrate. |
| Deodorant | Zinc oxide. Zinc ricinoleate. 2-Ethyl-1,3-hexanediol. Hexachlorophene. The product sold under the brand name "IRGASAN DP 300". |
| Anti dandruff | Octopyrox. Omadines. Coal tar. 1-Hydroxy-4-methyl-6(2,4,4-trimethylpentyl)-2-2(1H)-pyridinone. Selenium sulphide. |
| Anti-hair loss | Glucuronidonase inhibitors. Mucopolysaccharides. Methyl or hexyl nicotinate. Forskolin. Minoxidil. Xanthines. Retinoids. |
| Hair colorant | Oxidation bases and couplers. Direct dyes. Self-oxidizing dyes. |
| Hair bleaching agent | Hydrogen peroxide. |

TABLE I-continued

| FUNCTION | ACTIVE AGENTS WHICH ARE USABLE |
| --- | --- |
| Reducing agent for permanent-waving | Thioglycolic acid. Cysteine. Cysteamine. N-Acetylcysteine. N-Acetylcysteamine. Glycerol thioglycolate. |
| Skin and hair conditioner | Cationic polymers, cations. |

In addition to the active agents, the compositions can also contain formulation adjuvants such as preservatives, pigments, perfumes, pH agents or gelling agents other than those that form the subject of the invention.

The examples given below, by way of illustration and without implied limitation, will enable a better understanding of the invention to be gained.

EXAMPLE 1

Comparative Experiments

In this experiment, the stabilizing power of different stabilizing agents with respect to vesicles of soya bean lecithin was compared.

A—Preparation of the dispersion of stabilized vesicles

Vesicles were prepared from soya bean lecithin sold under the tradename "NATIPIDE II" by the company "NATTERMANN", by dispersion of 25% by weight of "NATIPIDE II" in distilled water at a temperature of 25° C. After 30 min of moderate stirring with a bar magnet, a dispersion was obtained, in an aqueous phase, of vesicles whose average size, measured using an "AMTECH BI 90" laser granulometer, is 200 nm with a polydispersity of 0.1. Independently, a solution containing 1% by weight of stabilizing agent in distilled water was prepared. The dispersion of vesicles and the solution of stabilizing agent were mixed so as to have a composition containing (by weight) 5% of soya bean lecithin and 0.1% of stabilizing agent. Mixing is performed in the course of 1 hour with moderate stirring using a bar magnet.

B—Test

A surfactant is then added at a temperature above the melting point of the surfactant, so as to have a final concentration of 1% by weight of surfactant in the mixture. The mixture is then agitated vigorously for 30 seconds using a "VORTEX" type homogenizer. After returning to room temperature, each mixture is subjected for 3 minutes to the action of ultrasound generated by the microprobe of a "BRANSON" type B 30 apparatus with the following setting:

working cycle: 50% power: position 6.

The temperature of the mixture is maintained close to room temperature during the action of the ultrasound using a bath of ice-cold water.

The turbidity of each mixture is then measured, after dilution to 1/150, at a wavelength of 400 nm using a UV/visible spectrophotometer. Under the action of the surfactants, the turbidity falls.

Measurements were performed with the following surfactants:

"BRIJ 72", alcohol bearing 2 ethylene oxide units, marketed by the company "ICI";

"TWEEN 60", polysorbate marketed by the company "ICI";

"TWEEN 20", polysorbate marketed by the company "ICI";

"LSS", sodium lauryl sulphate marketed by the company "RHONE-POULENC";

"PF 68", polyoxyethylene/polyoxypropylene copolymer marketed by the company "ICI";

"MYRJ 52", polyoxyethylene stearate marketed by the company "ICI";

"ARLAMOL E", polypropylenated alcohol marketed by the company "ICI";

"TEGIN 90", glycerol stearate marketed by the company "GOLDSCHMIDT".

For each surfactant, the experiments were performed without addition of a stabilizing agent (non-stabilized vesicles) and with the following stabilizing agents:

1) Compounds not forming part of the invention:

Chitosan,

High molecular weight DNA marketed by "JAVENECH",

Sodium alginate,

Gum arabic,

"ETICANE 3" (mixture of atelocollagen and glyco—aminoglycan) marketed by the company "BIOETICA", 2) Compounds forming part of the invention:

Propylene glycol alginates esterified to the extent of 80–85%, marketed by the company "KELCO" under the names "KELCOLOID O" and "MANUCOL ESTER E/PL", Gellan gums marketed under the names "KELCOGEL" and "KELCOGEL PC" by the company "KELCO", and Welan gum marketed under the reference "K1A96" by the company "KELCO".

Table II below gives, on the one hand the fall in turbidity in % calculated relative to a control containing neither surfactant nor stabilizer, and on the other hand the 80% protection index determined from the data for fall in turbidity. The 80% protection index corresponds to the ratio (number of surfactants tested in which the fall in turbidity was less than 20% relative to that of the control)/(total number of surfactants tested). The fall in turbidity given in Table II is the mean of three experiments.

TABLE II

| SURFACTANT | UNSTABILIZED VESICLES | CHITOSAN | DNA | Na+ ALGINATE | GUM ARABIC | ETICANE 3 |
| --- | --- | --- | --- | --- | --- | --- |
| BRIJ 72 | −40% ± 1 | D (1) | −31% ± 3 | −10% ± 0 | −11% ± 1 | −17% ± 2 |
| TWEEN 60 | −56% ± 2 | D | −34% ± 3 | −33% ± 2 | −31% ± 3 | −29% ± 2 |
| TWEEN 20 | −69% ± 2 | D | −60% ± 10 | −57% ± 3 | −54% ± 1 | −54% ± 3 |
| LSS | −68% ± 3 | D | −64% ± 2 | −59% ± 6 | −50% ± 1 | −58% ± 6 |
| PF 68 | −38% ± 1 | D | −39% ± 8 | −30% ± 9 | −16% ± 1 | −30% ± 1 |
| MYRJ 52 | −48% ± 2 | D | −48% ± 3 | −44% ± 5 | −41% ± 5 | −47% ± 1 |
| ARLAMOL E | −31% ± 3 | D | −11% ± 3 | −15% ± 1 | −13% ± 2 | −4% ± 4 |
| GLYCEROL STEARATE | −19% ± 1 | D | −18% ± 1 | −6% ± 3 | −6% ± 6 | −11% ± 2 |
| 80% PROTECTION INDEX | | 0/8 | 0/8 | 1/8 | 0/8 | 1/8 |

| SURFACTANT | KELCO-LOID O | KELCOGEL | WELAN GUM | MANUCOL ESTER E/PL | KELCO GEL PC |
| --- | --- | --- | --- | --- | --- |
| BRIJ 72 | +8% ± 3 | 0% ± 1 | +7% ± 1 | +5% ± 1 | +5% ± 3 |
| TWEEN 60 | +4% ± 5 | 0% ± 1 | −2% ± 3 | 0% ± 1 | +5% ± 1 |
| TWEEN 20 | 0% ± 7 | 0% ± 8 | −10% ± 3 | −14% ± 2 | −5% ± 4 |
| LSS | −6% ± 8 | −7% ± 8 | −8% ± 2 | −13% ± 2 | −5% ± 4 |
| PF 68 | 0% ± 1 | +0% ± 1 | +3% ± 1 | 0% ± 2 | +1% ± 1 |
| MYRJ 52 | −5% ± 2 | −7% ± 3 | +4% ± 2 | −3% ± 3 | +1% ± 1 |
| ARLAMOL E | +2% ± 2 | +3% ± 2 | — | — | — |
| GLYCEROL STEARATE | −2% ± 2 | −2% ± 3 | — | — | — |
| 80% PROTECTION INDEX | 8/8 | 8/8 | 6/6 | 6/6 | 6/6 |

(1): D destabilization of the vesicles; flocculation in irreversible clumps; crystals and growth.

EXAMPLE 2

In this example, the same experiments as in Example 1 were performed with variable doses of stabilizing agents according to the invention. The results are collated in Table III below.

These experiments show that with a concentration of stabilizing agent according to the invention of 0.10%, that is to say a weight proportion (stabilizing agent/lipid phase) of 2%, excellent stabilization results are obtained, and that with concentrations of 0.05 and 0.01%, that is to say with a weight proportion of 1 and 0.2% relative to the vesicular lipid phase, substantial protection is still obtained.

TABLE III

| | KELCOLOID O | | | KELCOGEL | | | UNSTABILIZED VESICLES |
| --- | --- | --- | --- | --- | --- | --- | --- |
| SURFACTANT | WEIGHT PROPORTION RELATIVE TO THE TOTAL WEIGHT OF THE COMPOSITION | | | | | | |
| | 1% | 0.10% | 0.05% | 0.01% | 0.10% | 0.05% | 0.01% | 0% |
| BRIJ 72 | +8% ± 3 | −1% ± 1 | 0% | 0% ± 1 | 0% | 0% | −39% ± 2 |
| TWEEN 60 | +4% ± 5 | −9% ± 1 | −13% ± 2 | 0% ± 1 | −8% ± 1 | −15% ± 2 | −51 ± 1 |

TABLE III-continued

| SURFACTANT | KELCOLOID O | | | KELCOGEL | | | UNSTABILIZED VESICLES |
|---|---|---|---|---|---|---|---|
| | WEIGHT PROPORTION RELATIVE TO THE TOTAL WEIGHT OF THE COMPOSITION | | | | | | |
| 1% | 0.10% | 0.05% | 0.01% | 0.10% | 0.05% | 0.01% | 0% |
| TWEEN 20 | 0% ± 7 | −26% ± 2 | −35% ± 2 | 0% ± 8 | −25% ± 1 | −42% ± 2 | −68% ± 1 |
| LSS | −6% ± 8 | −17% ± 1 | −32% ± 2 | −7% ± 8 | −12% ± 3 | −33% ± 2 | −66% ± 3 |
| PF 68 | 0% ± 1 | +1% ± 1 | −6% ± 1 | 0% ± 1 | 0% ± 1 | −5% ± 4 | −36% ± 1 |
| MYRJ 52 | −5% ± 2 | −5% ± 4 | −14% ± 1 | −7% ± 3 | −5% ± 2 | −22% ± 1 | −52% ± 1 |

EXAMPLE 3

In this example, the same experiment as that carried out in Example 1 was performed with vesicles of nonionic lipid.

A—Preparation of the dispersion of stabilized vesicles

Vesicles were prepared from:

a nonionic amphiphilic lipid of formula (A) below:

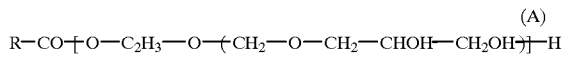

(A)

in which:

R represents an isostearyl (branched $C_{18}$) residue, and
—O—$C_2H_3$—O— represents the following structures, taken mixed or separately:

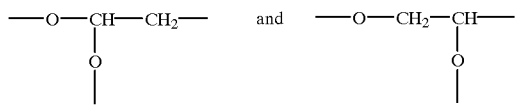

and L-N-stearoylglutamic acid monosodium salt, marketed by the company "AJINOMOTO" under the tradename "ACYLGLUTAMATE HS 11", in a 95:5 weight ratio.

These two lipid compounds are mixed by melting and then hydrated in the heated state (40° C.) with distilled water. The lipid mixture represents 5% by weight relative to the total weight of the dispersion. The temperature is brought down to 25° C. After 10 minutes of agitation using a "VIRTIS 60" type homogenizer at a speed of 40,000 rpm, a dispersion of vesicles in an aqueous phase was obtained. The size of the vesicles obtained is between 100 and 150 nm.

Independently, a solution containing 1% by weight of stabilizing agent in distilled water was prepared. The dispersion of vesicles and the solution of stabilizing agent were mixed so as to have a composition containing 5% by weight of the lipid mixture described above and 0.1% by weight of stabilizing agent. The mixing is performed in the course of 1 hour with moderate stirring using a bar magnet.

B—Test

The procedure thereafter is described in Example 1. The results appear in Table IV below:

TABLE IV

| Surfactant | Unstabilized vesicles | KELCOLOID O | KELCOGEL PC |
|---|---|---|---|
| TWEEN 60 | −11% | −5% ± 1 | +3% ± 3 |
| TWEEN 20 | −21% | −3% ± 1 | +2% ± 2 |
| LSS | −38% | −7% ± 1 | −7% ± 2 |
| PF 68 | −31% | 0% ± 1 | 0% ± 1 |

TABLE IV-continued

| Surfactant | Unstabilized vesicles | KELCOLOID O | KELCOGEL PC |
|---|---|---|---|
| MYRJ 52 | −35% | −5% ± 2 | −4% ± 1 |
| 80% protection | | 6/6 | 6/6 |

EXAMPLE 4

Oil-in-Water (O/W) Type Emulsion

In a 200-ml beaker:

5 g of cetyl alcohol, 3 g of a mixture of glycerol mono- and distearates marketed under the trade name "GELEOL COPEAUX", 3 g of polyoxyethylene stearate marketed under the tradename "MYRJ 53" by the company "ICI"

are dissolved in 24 g of liquid paraffin heated to a temperature of 65° C.

After the temperature has been brought down to 50° C., an aqueous phase at the same temperature, consisting of a solution of 0.3 g of the preservative mixture marketed under the tradename "ELASTAB 4112" by the company "LSN" in 54.7 g of water, is added with agitation imparted by a "MORITZ" homogenizer. Homogenization is maintained during cooling of the product to room temperature. A suspension of vesicles consisting of:

2.5 g of soya bean lecithin marketed under the tradename "NAPTIPIDE II" by the company "NATTERMAN", 7.49 g of water, 0.01 g of propylene glycol alginate marketed by the company "KELCO" under the tradename "KELCOLOID O"

is then added.

100 g of a thick cream intended for the care of dry skins are thereby obtained. The presence of vesicles after 3 months of storage was established by light microscopy.

EXAMPLE 5

Water-in-Oil (W/O) Type Emulsion

In a 200-ml glass beaker, the following are mixed at a temperature of 85° C. using a "MORITZ" type homogenizer:

5.7 g of a mixture of magnesium lanolate and liquid paraffin (50:50) marketed under the tradename "MEXANYL 60" the company "CHIMEX", 6.65 g of hydrogenated lanolin marketed under the tradename "SUPERSAT" by the company "RITA", and 2.0 g of 2-ethylhexyl ether of the ester of glycerol and palmitic acid (octoxyglyceryl palmitate), marketed under the tradename "MEXANYL GP" by the company "CHIMEX".

After homogenization, this first mixture is dissolved in a second mixture consisting of:

3 g of Purcellin oil of low solidification point, 3 g of a mixture of lanolin alcohol and liquid paraffin (15:85), marketed under the tradename "LIQUIDE BASE CB 1145" by the company "CRODA", 4.75 g of isopropyl palmitate, 7.9 g of liquid paraffin, 15 g of white soft paraffin, and 0.4 g of perhydrosqualene.

These two mixtures are homogenized at a temperature of 80° C. and then cooled to 40° C.

With agitation and at a temperature of 40° C., the aqueous phase consisting of the mixture of a solution of:

0.25 g of the mixture of preservatives marketed under the tradename "ELASTAB 4110" by the company "LSN" in 39.9 g of water, and 10 g of a vesicular dispersion consisting of:
  2.5 g of soya bean lecithin marketed under the tradename "NATIPIDE II" by the company "NATTERMAN".
  0.02 g of gellan gum marketed under the tradename "KELCOGEL PC" by the company "KELCO", and
  7.8 g of water, is then introduced.

Stirring is maintained for 20 minutes, and the mixture composed of the following is then added:

0.3 g of a preservative marketed under the tradename "GERMAL 115", and 0.35 g of water.

After returning to room temperature, the product obtained is transferred to a triple roll mill. A thick, smooth, white cream intended for the care of very dry skins is thereby obtained. The presence of vesicles after 3 months of storage was established by light microscopy.

EXAMPLE 6

Very Gentle Toilet Milk

In a 200-ml beaker:

2.8 g of glyceryl stearate marketed under the tradename "SIMULSOL 165" by the company "SEPPIC", 0.75 g of stearyl alcohol, are dissolved in a mixture of oils brought to 65° C. and composed of:

12 g of liquid paraffin, 0.5 g of lanolin oil marketed under the tradename "ARGONOL 60" by the company "WESTBROOCK", 2 g of sweet almond oil marketed by the company "SICTIA", 0.05 g of propyl para-hydroxybenzoate.

An aqueous phase at the same temperature, consisting of a solution of:

0.2 g of methyl para-hydroxybenzoate, 5 g of glycerol, 0.05 g of preservative marketed under the tradename "GERMAL 115", 0.1 g of acrylic acid homopolymer crosslinked with a pentaerythritol allyl ether or a sucrose allyl ether, marketed under the tradename "CARBOPOL 941" by the company "GOODRICH", 0.13 g of triethanolamine, and 66.42 g of water, is added with agitation imparted by a "MORITZ" homogenizer.

Homogenization is maintained for 20 minutes, and the formula is then agitated at a slow speed of the blades using a "RAYNER" type agitator until it has cooled completely. A vesicular dispersion consisting of the following is then added with reduced agitation:

2.5 g of soya bean lecithin marketed under the tradename "NATIPIDE II" by the company "NATTERMAN", 7.49 g of water, 0.01 g of propylene glycol alginate marketed under the tradename "MANUCOL ESTER E/PL" by the company "KELCO".

A very gentle white milk is then obtained. The presence of vesicles after 3 months of storage was established by light microscopy.

EXAMPLE 7

Night Cream (W/O)

In a 200-ml beaker, the following are dissolved in 20 g of liquid paraffin at 65° C.:

5 g of sorbitan isostearate marketed under the tradename "ARLACEL 987" by the company "ICI", 1.3 g of wax marketed under the tradename "DEA WAX 74181" by the company "CONDEA", 1.5 g of paraffin marketed under the tradename "CERAFINE 56/58" by the company "CERESINE", 5 g of a mixture of triglycerides of capric and caprylic acids, stearalconium hectorite and propylene carbonate, marketed under the tradename "MIGLYOL GEL B" by the company "HULS", 0.2 g of propyl para-hydroxybenzoate.

With agitation using a "MORITZ" type homogenizer and at 40° C., an aqueous phase consisting of the mixture of:

3 g of glycerol, 0.5 g of magnesium sulphate ($7H_2O$), 0.25 g of a preservative marketed under the tradename "GERMAL 115", 0.2 g of methyl para-hydroxybenzoate, in 54.55 g of water is then introduced, as well as a vesicular dispersion consisting of:

2.5 g of soya bean lecithin marketed under the tradename "NATIPIDE II" by the company "NATTERMAN", 7.49 g of water, 0.01 g of welan gum marketed under the tradename "K1A96" by the company "KELCO".

A thick, smooth, white cream intended for very dry skins is then obtained. The presence of vesicles after 3 months of storage was established by light microscopy.

EXAMPLE 8

Hydrating Day Cream (O/W emulsion)

In a 200-ml beaker, the following are dissolved in 18 g of liquid paraffin at 80° C.:

7 g of beeswax, 2 g of glyceryl stearate marketed under the tradename "TEGIN" by the company "GOLDSCHMIDT", 4 g of lanolin oil marketed under the tradename "AMERCHOL L101" by the company "AMERCHOL", 5 g of isopropyl myristate, 0.5 g of potassium cetyl phosphate marketed under the tradename "AMPHISOL K" by the company "GIVAUDAN-ROURE".

An aqueous phase at the same temperature, consisting of:

0.2 g of methyl para-hydroxybenzoate, 0.3 g of crosslinked acrylic polymer marketed under the tradename "CARBOMER 940" by the company "GOODRICH", 5 g of glycerol, 0.3 g of preservative marketed under the tradename "GERMAL 115", 0.3 g of triethanolamine, 47.4 g of water, is added with agitation imparted by a "MORITZ" homogenizer.

Agitation is maintained until 25° C. is reached, and a vesicular dispersion composed of:

0.9 g of the nonionic amphiphilic lipid of formula (A) of Example 3, 0.1 g of "ACYL GLUTAMATE HS 11" marketed by the company "AJINOMOTO", 0.02 g of gellan gum marketed under the name "KELCO-GEL" by the company "KELCO", 8.98 g of water, is then added to it with agitation corresponding to a slow speed of the blades of a "RAYNERI" type agitator.

After complete dispersion, a white cream for the daily care of dry skins is obtained. The presence of vesicles after 3 months of storage was established by light microscopy.

EXAMPLE 9

Cream for Dry Skins (O/W Emulsion)

In a 200-ml beaker:

5 g of cetyl alcohol, 3 g of a mixture of glycerol mono- and distearates, marketed under the tradename "GELEOL COPEAUX", 3 g of polyoxyethylene stearate marketed under the tradename "MYRJ 53" by the company "ICI" are dissolved in 24 g of liquid paraffin heated to a temperature of 65° C.

After the temperature has been brought down to 50° C., an aqueous phase at the same temperature, consisting of a solution of 0.3 g of the preservative mixture marketed under the tradename "ELASTAB 4112" by the company "LSN" in 54.7 g of water, is added with agitation imparted by a "MORITZ" homogenizer. Homogenization is maintained during cooling of the product at room temperature. A suspension of vesicles consisting of:

2.5 g of soya bean lecithin marketed under the tradename "NATIPIDE II" by the company "NATTERMAN", 7.49 g of water, 0.01 g of glycerol alginate marketed by the company "KELCO", is then added.

100 g of a thick cream intended for the care of dry skins are thereby obtained. The presence of vesicles after 3 months of storage was established by light microscopy.

We claim:

1. A process for the stabilization of vesicles formed from a lipid-phase membrane containing at least one ionic or nonionic amphiphilic lipid or a mixture thereof, said process comprising encapsulating an aqueous phase, in the form of a dispersion in an aqueous phase, adding at least one stabilizing agent to said aqueous dispersion phase, said stabilizing agent being selected from the group consisting of a glycerol alginate, a propylene glycol alginate, gellan gum and welan gum and being present in an amount effective so as to stabilize said vesicles against surfactants and, when present, a fatty phase.

2. The process of claim 1 wherein said stabilizing agent is an alginate esterified to the extent of more than 60 percent with propylene glycol or glycerol.

3. The process of claim 1 wherein said stabilizing agent is employed in an amount ranging from 0.1 to 20 percent by weight relative to the weight of the vesicular lipid phase.

4. The process of claim 1 wherein said stabilizing agent is employed in an amount ranging from 0.2 to 10 percent by weight relative to the weight of the vesicular lipid phase.

5. The process of claim 1 wherein the composition contains up to 20 weight percent of a surfactant relative to the total weight of the composition.

6. The process of claim 1 wherein the aqueous dispersion phase is combined with a fatty phase, said fatty phase representing up to 50 percent by weight of the aqueous dispersion phase.

7. A composition for topical application to the skin comprising (a) a dispersion in an aqueous phase of vesicles formed from a lipid-phase membrane containing at least one ionic amphiphilic lipid or a nonionic amphiphilic lipid or a mixture thereof, said lipid encapsulating a liquid phase and at least one stabilizing agent to stabilize said vesicles, said stabilizing agent being selected from the group consisting of a glycerol alginate, a propylene glycol alginate, gellan gum and welan gum and being present in an amount effective so as to stabilize said vesicles against surfactants.

8. The composition of claim 7 wherein said stabilizing agent is present in an amount ranging from 0.1 to 20 percent by weight relative to the weight of the vesicular lipid phase.

9. The composition of claim 7 wherein said stabilizing agent is present in an amount ranging from 0.2 to 10 percent by weight relative to the weight of the vesicular lipid phase.

10. The composition of claim 7 which contains from 1 to 20 percent by weight of a surfactant relative to the total weight of said composition.

11. The composition of claim 10 wherein said surfactant is selected from the group consisting of a sodium alkyl sulphate, a polyol ester, an oxyethylenated polyol ester, a polyoxyethylenated alcohol, a polypropylenated alcohol and a polyoxyethylene/polyoxypropylene copolymer.

12. The composition of claim 7 wherein said vesicular lipid phase comprises at least one lipid selected from the group consisting of:

(A) a nonionic lipid selected from the group consisting of
(1) linear or branched glycerol derivative of the formula

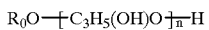

(IV)

wherein

—$C_3H_5(OH)O$— represents, separately or in admixture,

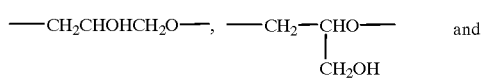

-continued

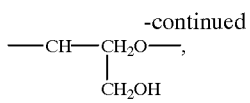

$\bar{n}$ has an average statistical value between 1 and 6 or, alternatively, n=1 or 2 and —$C_3H_5(OH)O$— is then represented by the structure, —$CH_2CHOH$—$CH_2O$—;

$R_0$ represents
(a) a saturated or unsaturated, linear or branched aliphatic chain containing from 12 to 30 carbon atoms; or a hydrocarbon radical of a lanolin alcohol; or a long-chain alphadiol residue;
(b) a residue $R_1CO$, wherein $R_1$ is a linear or branched $C_{11}$–$C_{29}$ aliphatic radical;
(c) a residue having the formula

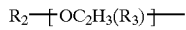

wherein $R_2$ can have the meaning (a) or (b) set forth for $R_0$; and $OC_2H_3(R_3)$ represents separately or in admixture

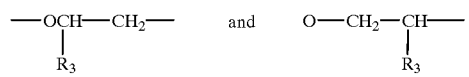

wherein $R_3$ has the meaning (a) given for $R_0$;
(2) a linear or branched polyglycerol ether containing two fatty chains,
(3) a fatty-chain diol;
(4) a fatty alcohol, oxyethylenated or not, a sterol or phytosterol, oxyethylenated or not;
(5) a polyether or polyester, oxyethylenated or not with the proviso that the ethylene oxide sequence is linear or cyclic;
(6) a glycolipid of natural or synthetic origin, an ether or ester of mono- or polysaccharides;
(7) a hydroxyamide having the formula

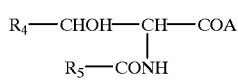 (V)

wherein $R_4$ represents a $C_7$–$C_{21}$ alkyl or alkenyl radical,
$R_5$ represents a saturated or unsaturated $C_7$–$C_{31}$ hydrocarbon radical,
COA represents a radical selected from the group consisting of

 (i)

wherein

B is an alkyl radical derived from a mono- or polyhydroxylated primary or secondary amine; and
$R_6$ represents hydrogen, methyl, ethyl or hydroxyethyl; and (ii) —COOZ wherein Z represents the residue of a $C_3$–$C_7$ polyol;
(8) a natural or synthetic ceramide;
(9) a dihydroxyalkylamine or an oxyethylenated fatty amine;
(10) a glycerol derivative having the formula:

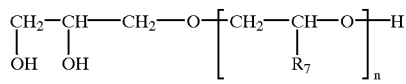 (VI)

wherein $R_7$ represents a linear $C_{14}$–$C_{18}$ alkyl or $CH_2A$ wherein A is $OR_{14}$,
$R_{14}$ represents linear $C_{10}$–$C_{18}$ alkyl,
n represents an average statistical value greater than 1 and equal to not more than 3, and when $R_7$=—$CH_2A$, n can also represent an actual, non-statistical value equal to 2;
(B) an ionic amphiphilic lipid selected from the group consisting of
(1) an anionic amphiphilic lipid selected from the group consisting of
(a) a natural phospholipid, chemically or enzymatically modified, phospholipids and synthetic phospholipids,
(b) anionic compounds having the formula:

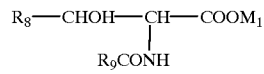 (VII)

wherein $R_8$ represents $C_7$–$C_{21}$ alkyl or alkenyl,
$R_9$ represents a saturated or unsaturated $C_7$–$C_{31}$ hydrocarbon radical, and
$M_1$ represents H, Na, K, $NH_4$ or a substituted ammonium ion derived from an amine;
(2) an anionic compound selected from the group consisting of
a phosphoric ester of a fatty alcohol,
a heptylnonylbenzenesulphonic acid,
cholesterol acid sulphate,
an alkali metal salt of cholesterol acid sulphate,
cholesterol acid phosphate,
an alkali metal salt of cholesterol acid phosphate,
a lysolecithin,
an alkyl sulphate and
a ganglioside;
(3) a cationic amphiphilic lipid selected from the group consisting of
(a) a cationic compound being a quaternary ammonium derivative having the formula

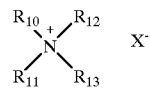 (VIII)

wherein $R_{10}$ and $R_{11}$, identical or different, represent $C_{12}$–$C_{20}$ alkyl and
$R_{12}$ and $R_{13}$, identical or different, represent $C_1$–$C_4$ alkyl;

(b) a long chain amine or a quaternary ammonium derivative thereof, an ester of a long-chain amino alcohol or a salt or quaternary ammonium derivative thereof and (c) a prepolymerized amphipilic lipid obtained from a polymerizable lipid or by reaction of an anionic lipid and a polymerizable cationic compound.

13. The composition of claim 7 wherein said aqueous dispersion phase comprises water or a mixture of water and at least one $C_1$–$C_7$ alcohol or a $C_1$–$C_5$ alkyl polyol or a mixture thereof.

14. The composition of claim 7 wherein a fatty phase is combined with the aqueous dispersion phase.

15. The composition of claim 14 wherein said fatty phase is in the form of a water-in-oil or oil-in-water emulsion, the aqueous phase of the emulsion comprising the aqueous phase of the dispersion of the vesicles.

16. The composition of claim 14 wherein said fatty phase comprises at least one compound selected from the group consisting of an animal oil, an animal fat, a vegetable oil, a vegetable fat, a natural or synthetic essential oil, a wax, a hydrocarbon, a halocarbon, a silicone, an ester of an inorganic acid and an alcohol, an ether and a polyether.

17. The composition of claim 14 wherein said fatty phase represents from 5 to 50 percent by weight of the total weight of said composition.

18. The composition of claim 7 containing at least one cosmetic active agent or at least one pharmaceutical active agent or a mixture thereof.

* * * * *